United States Patent
Furuishi et al.

(10) Patent No.: US 7,323,489 B2
(45) Date of Patent: Jan. 29, 2008

(54) PROLINE ESTER AND PREPARATION CONTAINING THE SAME FOR PERCUTANEOUS ADMINISTRATION

(75) Inventors: Takayuki Furuishi, Tokyo (JP); Kunihiro Minami, Fukushima (JP); Takayuki Minowa, Tokyo (JP); Miho Komine, Saitama (JP); Kunihiko Kimura, Fukushima (JP)

(73) Assignee: Toaeiyo Ltd., Tokyo (JP)

( * ) Notice: Subject to any disclaimer, the term of this patent is extended or adjusted under 35 U.S.C. 154(b) by 257 days.

(21) Appl. No.: 10/527,062

(22) PCT Filed: Sep. 8, 2003

(86) PCT No.: PCT/JP03/11420

§ 371 (c)(1), (2), (4) Date: Mar. 9, 2005

(87) PCT Pub. No.: WO2004/024754

PCT Pub. Date: Mar. 25, 2004

(65) Prior Publication Data

US 2005/0288232 A1    Dec. 29, 2005

(30) Foreign Application Priority Data

Sep. 11, 2002    (JP)    ............... 2002-265276

(51) Int. Cl.
*A61K 31/40* (2006.01)
*C07D 207/00* (2006.01)

(52) U.S. Cl. ...................... 514/423; 548/533

(58) Field of Classification Search ................ 548/533; 514/423

See application file for complete search history.

(56) References Cited

U.S. PATENT DOCUMENTS 4,374,829 A    2/1983    Harris et al.

FOREIGN PATENT DOCUMENTS

GB    2 207 129    1/1989
HU    196834    1/1989

OTHER PUBLICATIONS

Green, et al., Protective Groups in Organic Chemistry, Chapter 5: Protection for the Carboxy Group, 3rd., p. 382, 388 and 390 (1999).*

IP, Dominic P. et al. "Enalapril Maleate", Analytical Profiles of Drug Substances, vol. 16, pp. 207-243 1987.

Shiromani, P.K. et al. "Effect of Moisture on the Physical and Chemical Stability of Granulations and Tablets of the Anglotensin Converting Enzyme Inhibitor, Enalapril Maleate", Drug Development and Industrial Pharmacy, vol. 12, No. 14, pp. 2467-2480 1986.

Tocco, D.J. et al. "The Physiological Disposition and Metabolism of Enalapril Maleate in Laboratory Animals", Drug Metabolism and Disposition, vol. 10, No. 1, pp. 15-19 1982.

Kunihiro Mimami et al., "Enalaprilat Yudotai no Keihi Kyushu-sei ni Kansuru Kento", Dai 123 Kai The Pharmaceutical Society of Japan Nenkai Koen Yoshishu, No. 4, p. 106, Mar. 2003.

Li C. et al., The Study of Transdermal Administration of Ace Inhibitors and Improved Absorption of Their Prodrugs. Noven Pharmaceuticals, Inc., AAPS Annual Meeting and Exposiotion, 2000 & internet<URL:http://www.noven.com/NovenDoc3.pdf.>.

Fischer J. et al., Studies Relating to the Configuration and Conformation of 3, 5-Disubstituted Dihydro-2 (3H)-furanones. Liebigs Annalen der Chemie 1989, No. 11, pp. 1093 to 1097.

* cited by examiner

*Primary Examiner*—Rei-tsang Shiao
(74) *Attorney, Agent, or Firm*—Oblon, Spivak, McClelland, Maier & Neustadt, P.C.

(57) ABSTRACT

A proline ester represented by the following formula (I):

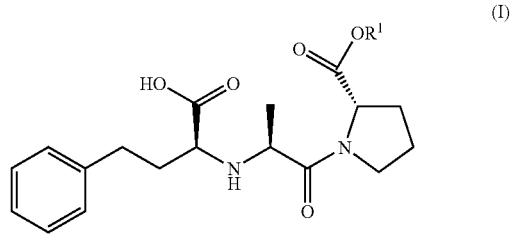

wherein $R^1$ represents a hydroxy-lower alkyl group, a lower alkoxy-lower alkyl group, or a lower alkoxy-lower alkoxy-lower alkyl group or a pharmaceutically acceptable salt thereof.

The proline ester (I) of the present invention and a pharmaceutically acceptable salt thereof are useful as a prodrug of enalaprilat, which is a medicine useful for preventing or treating circulatory diseases such as hypertension, cardiac diseases (e.g., cardiac hypertrophy, cardiac failure, and myocardial infarct), nephritis, and apoplexy. Thus, a drug containing the ester or a salt thereof is preferably formulated to a percutaneous preparation, particularly a patch, from the viewpoint of medicinal activity and use.

12 Claims, No Drawings

PROLINE ESTER AND PREPARATION CONTAINING THE SAME FOR PERCUTANEOUS ADMINISTRATION

This application is a 371 of PCT/JP03/11420 filed on Sep. 8, 2003.

TECHNICAL FIELD

The present invention relates to a proline ester which is useful as a prodrug of enalaprilat, an agent useful in treatment of hypertension or cardiac failure, to drugs containing the ester, and to preparations containing the ester for percutaneous administration.

BACKGROUND ART

Currently, as agents for the treatment of hypertension, a variety of peroral preparations such as a calcium antagonist, an angiotensin-converting enzyme (ACE) inhibitor, and an angiotensin receptor antagonist are employed in clinical settings. However, not a small number of patients with hypertension tend to experience difficulty in swallowing or have disorders in the digestive tract, and in such cases, peroral administration encounters difficulty. Therefore, development of an antihypertensive agent that can be administered through a route other than peroral route has been awaited. In general, use of a percutaneous preparation is suitable means for treating patients having difficulty in peroral administration, since a drug is absorbed through the skin. However, an antihypertensive agent in the form of percutaneous preparation has not become clinically available due to poor percutaneous absorbability, etc.

Meanwhile, enalapril in the form of a peroral agent is widely used in clinical settings as an antihypertensive agent having an ACE inhibitory effect. Enalapril is a prodrug of enalaprilat, which is an active metabolite of enalapril. Enalapril is formed through ethyl-esterification of one of the two carboxyl groups which is present in the vicinity of the center of the enalaprilat molecule. When perorally administered, enalapril is absorbed via the digestive tract and metabolized in the liver, where it is converted to enalaprilat, which is useful as an ACE inhibitor exhibiting a therapeutic effect.

Enalapril and enalaprilat are percutaneously absorbable. However, these compounds serving as active ingredients contained in a percutaneous preparation exhibit very poor physicochemical stability and therefore, they have not been successfully formed into percutaneous preparations. It has been proven that the poor stabilities of enalapril and enalaprilat are attributable to intramolecular ring formation through condensation of a secondary amine moiety of alanine with a carboxyl group linked to the proline ring (Analytical Profiles of Drug Substances, USA Academic press, Inc., 1987, Vol. 16, p. 207-244, Drug Development And Industrial Pharmacy, USA, Marcel Dekker, Inc., 1986, Vol. 12, 14, p. 2467-2480). Furthermore, there has been known that percutaneously absorbed enalapril is not converted to enalaprilat in the skin and also in the plasma (Drug Metabolism And Disposition, USA, The American Society for Pharmacology and Experimental Therapeutics, 1982, Vol. 10, 1, p. 15-19). Therefore, active enalaprilat is formed only when percutaneously absorbed enalapril is circulated to the liver and metabolized, which means that among other problems, a long period of time is required to express ACE inhibitory effect, and consistent therapeutic effect often fails to attain.

Research efforts have also been devoted to prodrug design; i.e., chemical modification of enalaprilat so as to change to a drug having physical properties suitable for percutaneous absorption while maintaining the intrinsic drug effect. In one report, a prodrug is formed through ethyl-esterification of both the carboxyl group present in the center of the enalapril molecule and the carboxyl group linked to the proline ring. The prodrug is known to exhibit enhanced percutaneous absorbability as compared with enalapril maleate (THE STUDY OF TRANSDERMAL ADMINISTRATION OF ACE INHIBITORS AND IMPROVED ABSORPTION OF THEIR PRODRUGS," [online], Nov. 2 (2000), Noven pharmaceuticals, Inc., AAPS Annual Meeting and Exposition (2000), internet<URL: http://www.noven.com/Noven Doc3.pdf>). However, although the ethyl ester moiety of the carboxyl group linked to the proline ring of the prodrug compound is hydrolyzed by an esterase present in the human skin at a hydrolyzation degree of 50% or more, the other ethyl ester moiety does not undergo hydrolysis. Therefore, similar to enalapril, the prodrug compound must be metabolized in the liver to form an active species, which is problematic.

DISCLOSURE OF THE INVENTION

In view of the foregoing, an object of the present invention is to provide a prodrug of enalaprilat which exhibits excellent percutaneous absorbability and physicochemical stability and which is readily converted to enalaprilat during the course of percutaneous absorption, so as to use enalaprilat via percutaneous absorption in clinical treatments. Another object of the invention is to provide a drug containing the prodrug. Still another object of the invention is to provide a percutaneous preparation containing the prodrug.

In an attempt to attain the above objects, the present inventors have synthesized and investigated a large number of candidate compounds serving as a prodrug of enalaprilat, and have found that a compound in which a carboxyl group on the proline ring of enalaprilat is esterified by a lower alkyl group having a specific substituent exhibits excellent physicochemical stability and skin-permeability and is effectively converted to enalaprilat during the course of skin permeation, thereby being useful for the prodrug, although a compound in which a carboxyl group on the proline ring of enalaprilat is esterified by an alkyl group exhibits no improvement in percutaneous absorbability. The present invention has been accomplished on the basis of this finding.

Accordingly, the present invention provides a proline ester represented by the following formula (I):

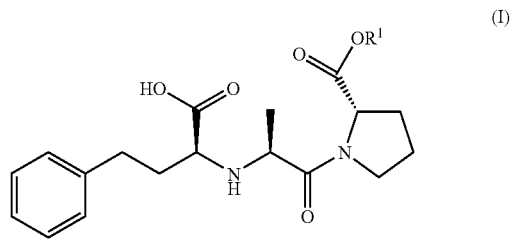

wherein $R^1$ represents a hydroxy-lower alkyl group, a lower alkoxy-lower alkyl group, or a lower alkoxy-lower alkoxy-lower alkyl group or a pharmaceutically acceptable salt thereof. The invention also provides a drug containing the ester or the salt thereof, particularly a percutaneous preparation.

The present invention also provides use, for producing a drug, of a proline ester represented by the above formula (I) or a pharmaceutically acceptable salt thereof.

The present invention further provides a method for treating a pathological condition affected or induced by activation of ACE, characterized by administering, to a patient in need thereof, a proline ester represented by the above formula (I) or a pharmaceutically acceptable salt thereof.

The proline ester (I) of the present invention and a pharmaceutically acceptable salt thereof are useful as a prodrug of enalaprilat, which is a drug useful for preventing or treating circulatory pathological conditions such as hypertension, cardiac diseases (e.g., cardiac hypertrophy, cardiac failure, and myocardial infarct), nephritis, and apoplexy. Thus, a drug containing the ester or a salt thereof is preferably formulated to a percutaneous preparation, particularly a patch, from the viewpoint of medicinal activity and use.

BEST MODES FOR CARRYING OUT THE INVENTION

Among substituents represented by R1 in formula (I) and R2 in the below mentioned formula (II), the term "lower alkyl" refers to a C1 to C6 linear or branched alkyl group, and the term "lower alkoxy" refers to a C1 to C4 linear or branched alkoxy group.

Examples of the hydroxy lower alkyl group represented by R1 include hydroxy-C1-6 alkyl groups such as hydroxymethyl, hydroxyethyl, hydroxypropyl, hydroxybutyl, hydroxypentyl, and hydroxyhexyl. Of these, 2-hydroxyethyl, 3-hydroxypropyl, and 4-hydroxybutyl are preferred.

Examples of the lower alkoxy-lower alkyl group represented by R1 include C1-4 alkoxy-C1-6 alkyl groups such as methoxyethyl, ethoxyethyl, propoxyethyl, isopropoxyethyl, butoxyethyl, isobutoxyethyl, sec-butoxyethyl, tert-butoxyethyl, and methoxypropyl. Of these, methoxyethyl is preferred.

Examples of the lower alkoxy-lower alkoxy-lower alkyl group represented by R1 include C1-4 alkoxy-C1-4 alkoxy-C1-6 alkyl groups such as methoxymethoxyethyl, methoxyethoxyethyl, and methoxymethoxybutyl. Of these, methoxyethoxyethyl is preferred.

The compound (I) of the present invention includes a hydrate thereof, solvates thereof, and all crystal forms thereof.

Examples of the pharmaceutically acceptable salt of the compound (I) of the present invention include inorganic acid salts such as hydrochlorides, hydrobromides, hydroiodides, nitrates, sulfates, and phosphates; organic acid salts such as acetates, propionates, trifluoroacetates, oxalates, fumarates, maleates, tartrates, citrates, succinates, malates, methanesulfonates, benzenesulfonates, and p-toluenesulfonates; alkali metal salts such as lithium salts, sodium salts, and potassium salts; and alkaline earth metal salts such as calcium salts and magnesium salts.

The compound (I) of the present invention is preferably 1-[N-[(1S)-1-Carboxy-3-phenylpropyl]-L-alanyl]-L-proline 2-hydroxyethyl ester, 1-[N-[(1S)-1-Carboxy-3-phenylpropyl]-L-alanyl]-L-proline 3-hydroxypropyl ester, 1-[N-[(1S)-1-Carboxy-3-phenylpropyl]-L-alanyl]-L-proline 4-hydroxybutyl ester, 1-[N-[(1S)-1-Carboxy-3-phenylpropyl]-L-alanyl]-L-proline 2-(2-methoxyethoxy)ethyl ester, or 1-[N-[(1S)-1-Carboxy-3-phenylpropyl]-L-alanyl]-L-proline 2-methoxyethyl ester.

The compound (I) of the present invention is produced through, for example, the following reaction scheme:

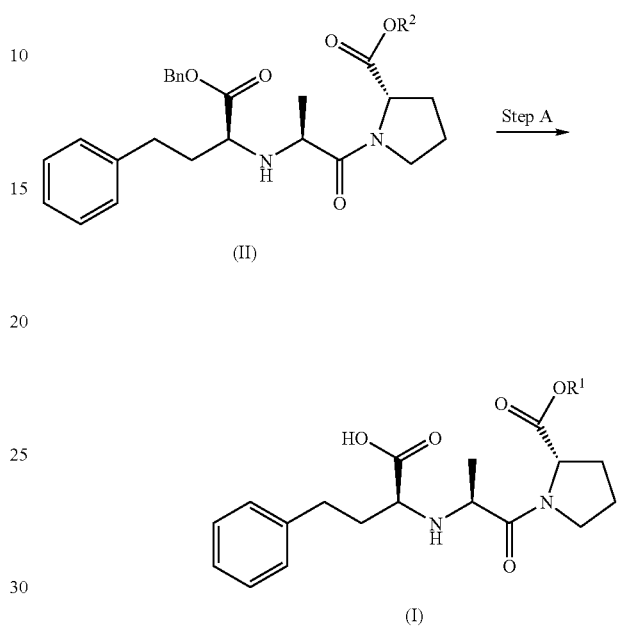

wherein $R^2$ represents a benzyloxy-lower alkyl group, a lower alkoxy-lower alkyl group, or a lower alkoxy-lower alkoxy-lower alkyl group, Bn represents a benzyl group, and $R^1$ has the same meaning as described above.

Specifically, the compound (I) of the present invention may be produced through deprotection of a compound (II) by removing a benzyl group with catalytic reduction (step A).

The reaction may be performed by subjecting the compound (II) to catalytic reduction in a solvent such as methanol, ethanol, ether, tetrahydrofuran, dioxane, N,N-dimethylformamide, or a solvent mixture thereof, in the presence of a metal catalyst such as palladium carbon, palladium black, tris(triphenylphosphine)rhodium chloride, or platinum oxide, at a temperature between 0° C. and the boiling point of the solvent, under hydrogen at normal or middle pressure. Through this reaction, a benzyl ester moiety or a benzyl ether moiety can be deprotected.

The compound (II), an intermediate compound for producing the compound (I) of the present invention, may be produced, through the following reaction scheme, by tert-butyl-esterifying enalapril (III) thereby preparing a compound (IV) (step B); selectively hydrolyzing the ethyl ester moiety of the compound (IV) thereby preparing compound (V) (step C); benzyl-esterifying the compound (V) thereby preparing compound (VI) (step D); hydrolyzing the tert-butyl ester moiety of the compound (VI) (step E), and reacting the resultant compound with $R^2OH$ (VIII):

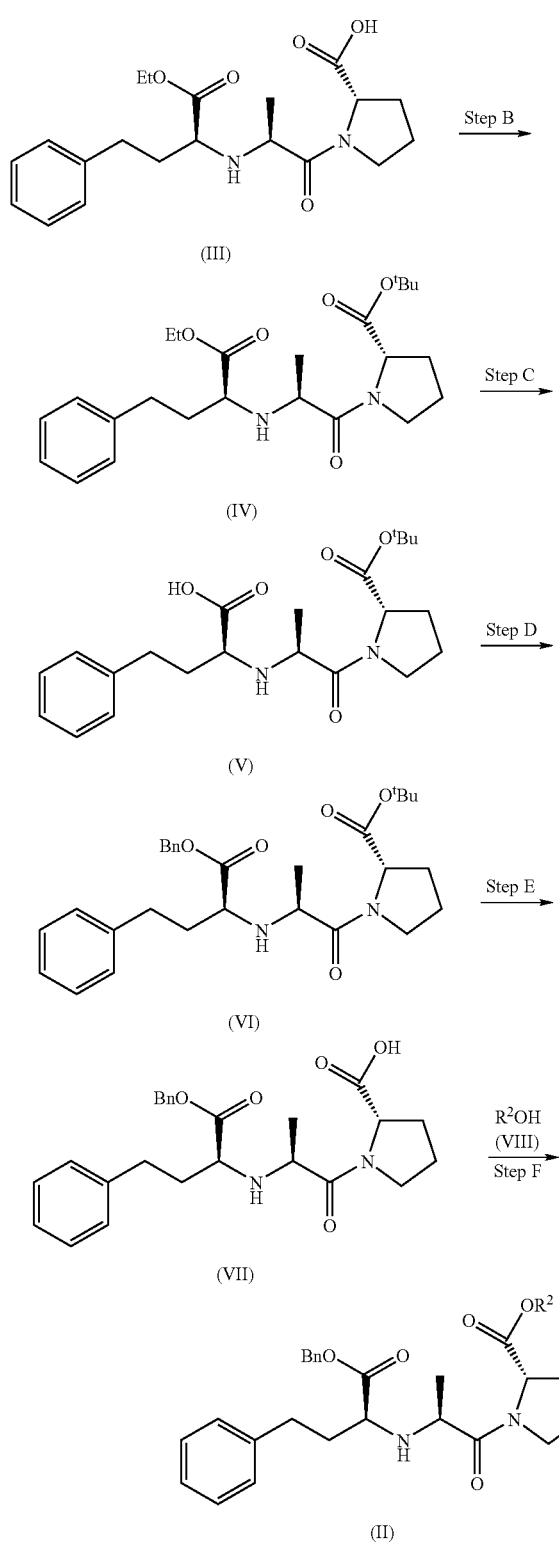

presence of an acid catalyst such as concentrated sulfuric acid or boron trifluoride diethyl etherate at a temperature between −78° C. and room temperature. In Step C, the ester moiety of the compound (IV) is hydrolyzed by use of an alkaline aqueous solution such as an aqueous sodium hydroxide solution or an aqueous potassium hydroxide solution. In Step D, the compound (V) is reacted with a benzyl halide in a solvent such as ether, tetrahydrofuran, dioxane, N,N-dimethylformamide, dimethylsulfoxide, dichloromethane, chloroform, or a solvent mixture thereof in the presence of a base such as sodium amide, lithium amide, sodium hydride, potassium carbonate, or potassium tert-butoxide at a temperature between 0° C. and the boiling point of the solvent. In Step E, the tert-butyl ester moiety of the compound (VI) is deprotected in a solvent such as ether, tetrahydrofuran, dioxane, dichloromethane, chloroform, or a solvent mixture thereof in the presence of an acid such as formic acid, acetic acid, trifluoroacetic acid, hydrochloric acid, or a hydrogen chloride-dioxane solution at a temperature between 0° C. and the boiling point of the solvent. In Step F, the compound (VII) is reacted with an alcohol (VIII) in a solvent such as benzene, toluene, xylene, or a solvent mixture thereof in the presence of an acid catalyst such as p-toluenesulfonic acid at the boiling point of the solvent.

Alternatively, the compound (II) may be prepared, through the following reaction scheme, by hydrolyzing a compound (IX) thereby preparing a compound (X) (step G); benzyl-esterifying the compound (X) thereby preparing a compound (XI) (step H); reacting the compound (XI) with an L-alanine tert-butyl ester thereby preparing a compound (XII) (step I), selectively hydrolyzing the tert-butyl ester moiety of the compound (XII) (step J), and subjecting the compound (XIII) to condensation with the compound (XIV) (step K):

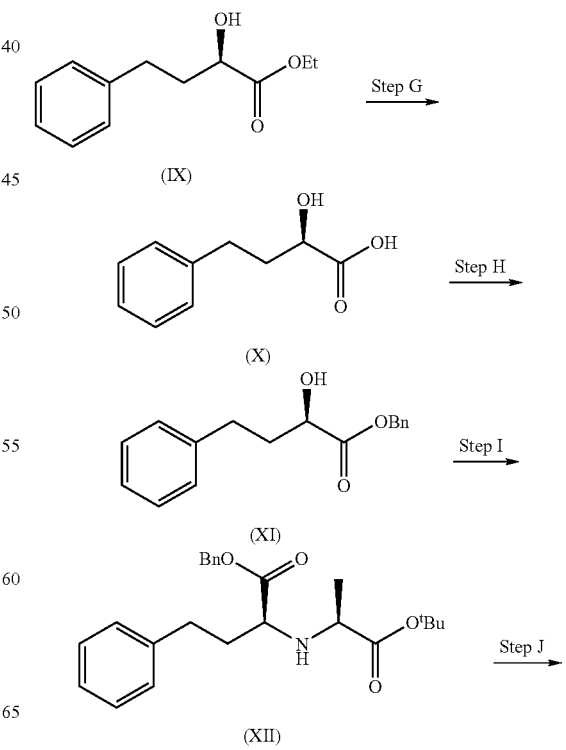

wherein $R^2$ and Bn have the same meanings as described above.

In Step B, enalapril (III) is reacted with isobutene in a solvent such as ether, tetrahydrofuran, dioxane, dichloromethane, chloroform, or a solvent mixture thereof in the

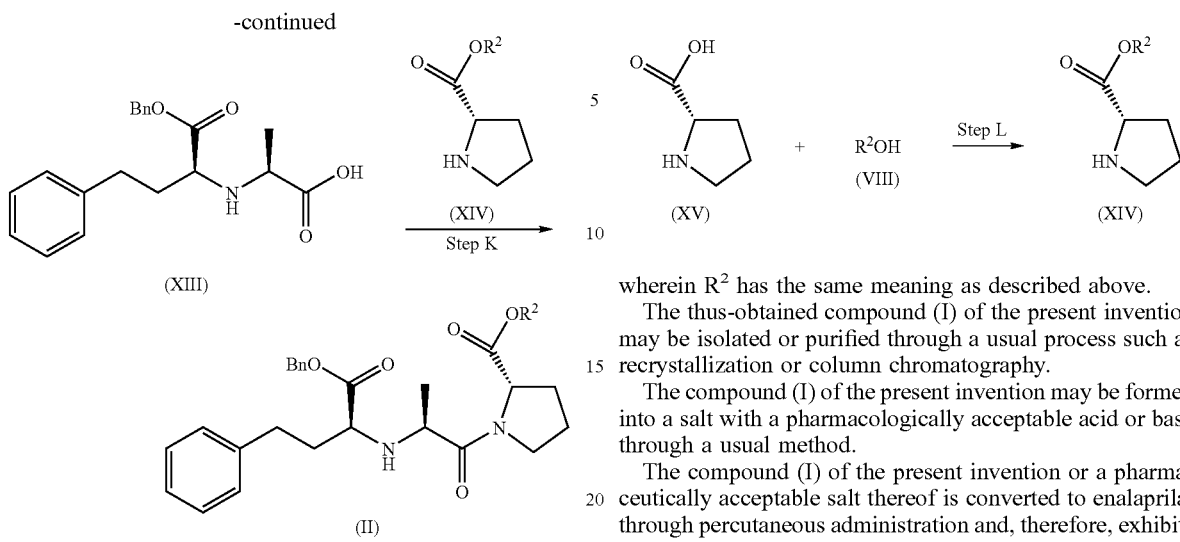

wherein $R^2$ and Bn have the same meanings as described above.

In the step G, the ester moiety of a compound (IX) is hydrolyzed by use of an alkaline aqueous solution such as an aqueous sodium hydroxide solution or an aqueous potassium hydroxide solution. In Step H, the compound (X) is reacted with a benzyl halide in a solvent such as ether, tetrahydrofuran, dioxane, N,N-dimethylformamide, dimethylsulfoxide, dichloromethane, chloroform, or a solvent mixture thereof in the presence of a base such as sodium amide, lithium amide, sodium hydride, potassium carbonate, potassium hydrogencarbonate, potassium tert-butoxide at a temperature between 0° C. and the boiling point of the solvent. In Step I, the compound (XI) is reacted with trifluoromethanesulfonic anhydride in a solvent such as dichloromethane or chloroform in the presence of 2,6-lutidine to thereby prepare a trifluoromethanesulfonic acid ester, and the ester is reacted with an L-alanine tert-butyl ester hydrochloride. In Step J, the tert-butyl ester moiety of the compound (XII) is deprotected in a solvent such as ether, tetrahydrofuran, dioxane, dichloromethane, chloroform, or a solvent mixture thereof in the presence of an acid such as formic acid, acetic acid, trifluoroacetic acid, hydrochloric acid, or a hydrogen chloride-dioxane solution at a temperature between 0° C. and the boiling point of the solvent. In Step K, the compound (XIII) is condensed with a compound (XIV) in a solvent such as ether, tetrahydrofuran, dioxane, N,N-dimethylformamide, dichloromethane, chloroform, benzene, toluene, or a solvent mixture thereof at a temperature between 0° C. and the boiling point of the solvent (if necessary, in the presence of a base such as triethylamine, ethyldiisopropylamine, or 1,8-diazabicyclo[5.4.0]undec-7-ene) by use of a condensing agent such as 1-hydroxy-1H-benzotriazole, N-hydroxysuccinimide, N,N'-dicyclohexylcarbodiimide, or 1-ethyl-3-(3-dimethylaminopropylcarbodiimide).

The compound (XIV) may be prepared by reacting proline (XV) with an alcohol (VIII) in a solvent such as benzene, toluene, xylene, or a solvent mixture thereof in the presence of an acid catalyst such as p-toluenesulfonic acid at the boiling point of the solvent (step L):

wherein $R^2$ has the same meaning as described above.

The thus-obtained compound (I) of the present invention may be isolated or purified through a usual process such as recrystallization or column chromatography.

The compound (I) of the present invention may be formed into a salt with a pharmacologically acceptable acid or base through a usual method.

The compound (I) of the present invention or a pharmaceutically acceptable salt thereof is converted to enalaprilat through percutaneous administration and, therefore, exhibits excellent ACE-inhibitory activity. By virtue of the activity, the compound (I) or a pharmaceutically acceptable salt thereof can be used for preventing or treating pathological conditions affected or induced by activation of ACE, for example, circulatory diseases such as hypertension, cardiac diseases (e.g., cardiac hypertrophy, cardiac failure, and myocardial infarct), nephritis, and apoplexy. Although the daily dose of compound (I) administered per adult may vary depending on the pathological conditions, body weight, and age of patients, and type of compound, etc., the dose is preferably about 1 to about 1,000 mg.

Preferably, the percutaneous preparation of the present invention further contains a percutaneous absorption enhancer for enhancing percutaneous absorbability. The percutaneous absorption enhancer may be selected from the group consisting of fatty acid esters and nonionic surfactants. These enhancers may be used singly or in combination of two or more species.

Examples of the fatty acid ester include fatty acid esters formed from a C6 to C22 fatty acid and a C1 to C12 alcohol. Examples of the C6 to C22 fatty acid include monocarboxylic acids such as caproic acid, enanthic acid, caprylic acid, capric acid, undecylenic acid, lauric acid, myristic acid, palmitic acid, margaric acid, stearic acid, oleic acid, and linoleic acid and dicarboxylic acids such as adipic acid and sebacic acid. Examples of the C1 to C12 alcohol include methanol, ethanol, propanol, isopropanol, butanol, tert-butanol, hexanol, octanol, and 1-octyl dodecanol. Thus, examples of the fatty acid esters include diisopropyl adipate, diethyl sebacate, isopropyl myristate, isopropyl palmitate, isopropyl stearate, butyl stearate, octyldodecyl myristate, butyl myristate, hexyl laurate, octyl palmitate, and ethyl oleate. Of these, isopropyl myristate, isopropyl palmitate, diethyl sebacate, and the like are preferred, with isopropyl myristate being particularly preferred.

Examples of the nonionic surfactant include polyoxyethylene alkyl ethers, polyoxyethylene alkyl aryl ethers, fatty acid amides, glycerin fatty acid esters, propylene glycol fatty acid esters, sorbitan fatty acid esters, polyoxyethylene sorbitan fatty acid esters, polyoxyethylene fatty acid esters, polyoxyethylene glycerin fatty acid esters, polyoxyethylene castor oil derivatives, block polymer type nonionic surfactants, and polyglycerin fatty acid esters. Of these, polyoxyethylene alkyl ethers, fatty acid amides, glycerin fatty acid esters, sorbitan fatty acid esters, and polyoxyethylene sorbitan fatty acid esters are preferred.

Examples of the polyoxyethylene alkyl ethers include polyoxyethylene cetyl ether, polyoxyethylene oleyl ether, and polyoxyethylene lauryl ether. Particularly, polyoxyethylene lauryl ether (lauromacrogol) is preferred.

Examples of the fatty acid amides include lauric acid monoethanolamide, lauric acid diethanolamide, and oleic acid diethanolamide. Particularly, lauric acid diethanolamide is preferred.

Examples of the glycerin fatty acid esters include glyceryl monocaprylate, glyceryl monolaurate, glyceryl monopalmitate, glyceryl monooleate, and glyceryl monostearate. Particularly, glyceryl monocaprylate and glyceryl monolaurate are preferred.

Examples of the sorbitan fatty acid esters include sorbitan monocaprylic acid ester, sorbitan monolauric acid ester, sorbitan monopalmitic acid ester, sorbitan monooleic acid ester, and sorbitan monostearic acid ester. Particularly, sorbitan monocaprylic acid ester is preferred.

Examples of the polyoxyethylene sorbitan fatty acid esters include polyoxyethylene sorbitan monooleic acid ester, polyoxyethylene sorbitan trioleic acid ester, and polyoxyethylene sorbitan monopalmitic acid ester. Particularly, polyoxyethylene sorbitan monooleic acid ester is preferred.

The percutaneous absorption enhancer is preferably selected from the group consisting of isopropyl myristate, lauromacrogol, lauric acid diethanolamide, glyceryl monocaprylate, glyceryl monolaurate, sorbitan monocaprylic acid ester, and polyoxyethylene sorbitan monooleic acid ester.

No particular limitation is imposed on the preparation form of the percutaneous preparation, and examples of the form include ointment, cream, patch, and lotion. Of these, patch is preferred from the viewpoint of use of patients.

The type of the patch may include a known support and a known adhesive layer, and may be produced by applying, to a surface of a support, an adhesive containing the compound of the present invention (I) or a salt thereof and an additive such as a percutaneous absorption enhancer, and cutting the coated support to pieces having predetermined sizes. The surface of the adhesive layer which is not in contact with the support may be coated with a protective member such as a peelable sheet. Alternatively, the surface may be protected by rolling the coated support.

Examples of the adhesive employed in the invention include an acrylic adhesive, a rubber adhesive, and a silicone adhesive, which exhibit pressure-sensitivity at ambient temperature.

The acrylic adhesive preferably contains a homopolymer, for example, comprised of a (meth)acrylic acid alkyl ester as a predominant component, or copolymer thereof with another comonomer (as used herein, the term "(meth)acrylic acid" refers to methacrylic acid or acrylic acid). Examples of the (meth)acrylic acid alkyl ester monomer include (meth)acrylic acid-2-ethylhexyl ester, (meth)acrylic acid ethyl ester, (meth)acrylic acid butyl ester, (meth)acrylic acid isobutyl ester, (meth)acrylic acid hexyl ester, (meth)acrylic acid octyl ester, (meth)acrylic acid decyl ester, (meth)acrylic acid isodecyl ester, (meth)acrylic acid lauryl ester, and (meth)acrylic acid stearyl ester. Examples of the comonomer include acrylic acid, methacrylic acid, maleic acid, fumaric acid, 2-hydroxyethyl(meth)acrylate, hydroxypropyl (meth)acrylate, acrylamide, dimethyl acrylamide, diethyl acrylamide, butoxymethyl acrylamide, ethoxymethyl acrylamide, N-vinyl-2-pyrrolidone, vinyl acetate, vinyl propionate, styrene, α-methylstyrene, vinyl chloride, acrylonitrile, ethylene, propylene, and butadiene.

No particular limitation is imposed on the type of the rubber adhesive, and examples include styrene-butadiene copolymer, styrene-isoprene copolymer, styrene-isoprene-styrene block copolymer, natural rubber, synthetic isoprene rubber, polyisobutylene, polyvinyl ether, polyurethane, polyisoprene, and polybutadiene.

No particular limitation is imposed on the silicone adhesive, and example include silicone rubber such as polyorganosiloxane.

Among them, styrene-isoprene-styrene block copolymer is particularly preferred, since the block polymer exhibits excellent compatibility with the compound (I) of the present invention and excellent physical properties for serving as a patch.

The support is preferably resistive to drug permeation. Examples of the support include resin films made of polyethylene terephthalate, cellulose acetate, ethyl cellulose, nylon, ethylene-vinyl acetate copolymer, polyethylene, or polyurethane. Since the support is required to have flexibility, the thickness of the support is generally 300 μm or less, preferably 2 to 100 μm or less.

The peelable sheet is required to be readily separated from the adhesive layer upon use. Thus, the peelable sheet is generally formed of a film coated with silicone on the side which is in contact with the adhesive layer. Examples of the film material include polyethylene terephthalate, polyvinyl chloride, polyvinylidene chloride, and polyester. A laminate film such as glassine paper sheet may also be used. The peelable sheet generally has a thickness of 1,000 μm or less, preferably 30 to 150 μm.

The patch contains the compound (I) of the present invention in an amount required for treatment. The compound (I) of the present invention or a salt thereof is preferably incorporated into the adhesive layer in an amount of 0.1 to 30 mass % with respect to the total mass of the adhesive layer in a dried state, more preferably 0.5 to 20 mass %. The adhesive layer preferably has a thickness of 10 to 400 μm.

The percutaneous absorption enhancer is preferably incorporated into the adhesive layer in an amount of 0.1 to 60 mass % with respect to the total mass of the adhesive layer in a dried state, more preferably 1 to 40 mass %. In the case of a fatty acid ester, the amount is preferably 1 to 40 mass %, and in the case of a non-ionic surfactant, the amount is preferably 1 to 20 mass %.

No particular limitation is imposed on the method for forming the adhesive layer of the patch, but a solution coating method is preferred. Specifically, an adhesive, a drug, an optional percutaneous absorption enhancer, and optional additives are mixed together, and the mixture is dispersed in an organic solvent. The obtained dispersion is applied to a surface of the support by use of an applicator, and the coating is dried to remove the solvent, thereby forming the adhesive layer. In an alternative method, the above dispersion is applied on a peelable sheet and, after drying, the coating is transferred to the support.

When the percutaneous preparation of the present invention is an ointment, a cream, or a lotion, examples of the base material include, but not limited to, hydrocarbons such as white petrolatum, liquid paraffin, paraffin, squalane, and plastibase, higher alcohols such as cetanol and stearyl alcohol, higher fatty acids such as isostearic acid, oleic acid, and lauric acid, thickeners such as carboxyvinyl polymer, carboxymethylcellulose, methylcellulose, hydroxypropylcellulose, hydroxypropylmethylcellulose, polyvinyl alcohol, polyacrylic acid, sodium polyacrylate, polyvinyl pyrrolidone, acacia, alginic acid, sodium alginate, and gelatin, and polyhydric alcohols such as glycerin, propyleneglycol, and 1,3-butyleneglycol.

The percutaneous preparation of the present invention may incorporate, in addition to the components described above, other additives such as anti-oxidants, excipients, solubilizing agents, antibacterial agents, and skin irritation reducing agents in accordance with needs. Examples of the anti-oxidant include vitamin E and vitamin C. Examples of the excipients include kaolin, bentonite, and titanium dioxide. Examples of the solubilizing agents include α-cyclodextrin, β-cyclodextrin, γ-cyclodextrin, hydroxypropyl-β-cyclodextrin, and sulfobutyl ether-β-cyclodextrin. Examples of the antibacterial agents include benzalkonium chloride, benzoic acid, and methyl parahydroxybenzoate. Examples of the skin irritation reducing agents include silicic acid anhydride. Moreover, absorption regulating agents may be incorporated. Examples of the absorption regulating agents include polyprenylazacycloalkanes (such as 1-dodecylazacycloheptan-2-one) and fats and oils (such as olive oil, castor oil, jojoba oil, corn germ oil, sunflower oil, coconut oil, squalane, squalene, orange oil, and mineral oil).

EXAMPLES

The present invention will next be described in more detail by way of Referential Examples, Examples, and Formulation Examples, which should not be construed as limiting the invention thereto.

Referential Example 1

1-[N-(1S)-1-Ethoxycarbonyl-3-phenylpropyl]-L-alanyl]-L-proline tert-butyl ester (compound (IV))

Enalapril maleate (5.0 g) was suspended in water (40 mL), and saturated aqueous sodium bicarbonate solution (60 mL) was added to the suspension, thereby forming a complete solution. The pH of the aqueous solution was adjusted to 4 to 5 with 10 w/v % hydrochloric acid. The solution was extracted with chloroform, and the obtained organic layer was dried over anhydrous sodium sulfate. The solvent was removed under reduced pressure, and the residue was dissolved in dioxane. To the solution, concentrated sulfuric acid (1.0 mL) and isobutene (30 mL) were added. The mixture was transferred to a sealable reactor, followed by closing the reactor, and stirred at room temperature for two days. The reaction mixture was neutralized with saturated aqueous sodium bicarbonate solution, and the mixture was extracted with ether. The obtained organic layer was washed with water and saturated brine and dried over anhydrous sodium sulfate. The solvent was removed under reduced pressure, and the residue was purified by silica gel column chromatography (hexane:ethyl acetate=1:1), to thereby yield 2.74 g of the title compound as a colorless oily substance.

$^1$H-NMR (CDCl$_3$) δ: 1.21-1.38 (6H, m), 1.45 (9H, s), 1.87-2.25 (7H, m), 2.59-2.80 (2H, m), 3.24 (1H, t, J=6.6 Hz), 3.43-3.60 (2H, m), 4.18 (2H, q, J=7.2 Hz), 4.41-4.46 (1H, m), 7.14-7.30 (5H, m). IR (neat) ν$_{max}$: 2977, 2932, 2875, 1737, 1650, 1453, 1422, 1367, 1154, 1094, 1031, 750, 701 cm$^{-1}$. MS m/z (ESI+): 433 (M+H)$^+$.

Referential Example 2

1-[N-[(1S)-1-Carboxy-3-phenylpropyl]-L-alanyl]-L-proline tert-butyl ester (compound (V))

The compound (IV) (2.0 g) was dissolved in methanol (15 mL), and, at 0° C., a 1 mol/L aqueous sodium hydroxide solution (15 mL) was added thereto, followed by stirring for three hours at room temperature. The reaction mixture was neutralized with 10 w/v % hydrochloric acid, and methanol was removed, followed by extraction with chloroform. The obtained organic layer was dried over anhydrous sodium sulfate. The solvent was removed under reduced pressure, to thereby yield 1.87 g of the title compound as a colorless amorphous substance.

$^1$H-NMR (CDCl$_3$) δ: 1.42 (9H, s), 1.47 (3H, d, J=6.8 Hz), 1.87-2.01 (3H, m), 2.10-2.25 (3H, m), 2.76-2.83 (2H, m), 3.33-3.61 (3H, m), 4.04-4.15 (1H, m), 4.36-4.41 (1H, m), 7.10-7.23 (5H, m). IR (KBr) ν$_{max}$: 3435, 2981, 1735, 1654, 1450, 1368, 1226, 1152, 1095, 1042, 849, 750, 701 cm$^{-1}$. MS m/z (ESI+): 405 (M+H)$^+$. [α]$_D$=−44.2° (CHCl$_3$, c:1.07).

Referential Example 3

1-[N-[(1S)-1-Benzyloxycarbonyl-3-phenylpropyl]-L-alanyl]-L-proline tert-butyl ester (compound (VI))

The compound (V) (1.47 g) was dissolved in N,N-dimethylformamide (7.0 mL), and benzyl bromide (684 mg) and potassium carbonate (502 mg) were added thereto, followed by stirring for one hour at room temperature. Water (70 mL) was added to the reaction mixture, and the resultant mixture was extracted with ethyl acetate. The obtained organic layer was washed with water and saturated brine and dried over anhydrous sodium sulfate. The solvent was removed under reduced pressure, and the residue was purified by silica gel column chromatography (hexane:ethyl acetate=1:1), to thereby yield 1.65 g of the title compound as a colorless oily substance.

$^1$H-NMR (CDCl$_3$) δ: 1.25 (3H, d, J=6.8 Hz), 1.43 (9H, s), 1.75-2.25 (7H, m), 3.20-3.52 (4H, m), 4.38 (1H, dd, J=3.6, 8.3 Hz), 5.13 (1H, d, J=12.1 Hz), 5.18 (1H, d, J=12.1 Hz), 7.05-7.47 (10H, m). IR (neat) ν$_{max}$: 2976, 1736, 1648, 1496, 1454, 1423, 1367, 1154, 750, 700 cm$^{-1}$. [α]$_D$=−86.4° (CHCl$_3$, c:1.39)

Referential Example 4

1-[(N-[(1S)-1-Benzyloxycarbonyl-3-phenylpropyl]-L-alanyl]-L-proline (compound (VII))

The compound (VI) (1.50 g) was dissolved in dichloromethane (6.0 mL), and at 0° C., trifluoroacetic acid (6.0 mL) was added dropwise thereto, followed by stirring for two hours at room temperature. After the solvent was removed under reduced pressure, the pH of the reaction mixture was shifted to an alkaline range with saturated aqueous sodium bicarbonate solution, and subsequently adjusted to 4 to 5 with 10 w/v % hydrochloric acid, followed by extraction with chloroform. The obtained organic layer was dried over anhydrous sodium sulfate, and the solvent was removed under reduced pressure. The residue was purified by silica gel column chromatography (chloroform:methanol=50:1), to thereby yield 1.09 g of the title compound as a colorless amorphous substance.

$^1$H-NMR (CDCl$_3$) δ: 1.23 (3H, d, J=6.8 Hz), 1.77-2.33 (6H, m), 2.55-2.78 (2H, m), 3.21-3.45 (3H, m), 3.50 (1H, q, J=6.8 Hz), 4.40-4.50 (1H, m), 5.11 (1H, d, J=12.1 Hz), 5.17 (1H, d, J=12.1 Hz), 7.06-7.46 (10H, m). IR (KBr) ν$_{max}$: 3448, 3030, 2954, 2879, 1736, 1638, 1497, 1454, 1382, 1191, 749, 698 cm$^{-1}$. [α]$_D$=−86.4° (CHCl$_3$, c:1.14)

Referential Example 5

1-[N-[(1S)-1-Benzyloxycarbonyl-3-phenylpropyl]-L-alanyl]-L-proline 2-benzyloxyethyl ester (compound (IIa))

The compound (VII) (1.06 g) was dissolved in benzene (5.0 mL), and 2-benzyloxyethanol (1.85 g) and p-toluenesulfonic acid monohydrate (555 mg) were added thereto, followed by stirring for three hours under reflux while generated water was removed by azeotropy. The solvent was removed, and ethyl acetate was added thereto. The mixture was washed with saturated aqueous sodium bicarbonate solution, water, and saturated brine and dried over anhydrous sodium sulfate. The solvent was removed under reduced pressure, and the residue was purified by silica gel column chromatography (hexane:ethyl acetate=1:1), to thereby yield 1.02 g of the title compound as a colorless oily substance.

$^1$H-NMR (CDCl$_3$) δ: 1.23 (3H, d, J=6.8 Hz), 1.70-2.35 (7H, m), 2.51-2.77 (2H, m), 3.20-3.76 (6H, m), 4.16-4.42 (2H, m), 4.46-4.58 (3H, m), 5.12 (1H, d, J=12.1 Hz), 5.17 (1H, d, J=12.1 Hz), 7.04-7.47 (15H, m). IR (neat) ν$_{max}$: 3474, 3325, 3062, 3029, 2953, 2874, 1742, 1645, 1496, 1454, 1424, 1366, 1277, 1184, 1028, 916, 746, 700 cm$^{-1}$. [α]$_D$=−67.6° (CHCl$_3$, c:1.27)

Referential Example 6

1-[N-[(1S)-1-Benzyloxycarbonyl-3-phenylpropyl]-L-alanyl]-L-proline 3-benzyloxypropyl ester (compound (IIb))

In the same manner as in Referential Example 5, 943 mg of the title compound was obtained as a colorless oily substance from 800 mg of the compound (VII) and 1.52 g of 3-benzyloxypropanol.

$^1$H-NMR (CDCl$_3$) δ: 1.23 (3H, d, J=6.8 Hz), 1.75-2.27 (9H, m), 2.54-2.73 (2H, m), 3.20-3.59 (6H, m), 4.09-4.29 (2H, m), 4.42-4.54 (1H, m), 4.48 (2H, s), 5.12 (1H, d, J=12.1 Hz), 5.17 (1H, d, J=12.1 Hz), 7.04-7.45 (15H, m). IR (neat) ν$_{max}$: 3473, 3322, 3061, 3029, 2956, 2871, 1740, 1646, 1496, 1454, 1423, 1364, 1277, 1182, 1096, 1046, 1029, 916, 741, 699 cm$^{-1}$. [α]$_D$=−67.3° (CHCl$_3$, c:1.02)

Referential Example 7

1-[N-[(1S)-1-Benzyloxycarbonyl-3-phenylpropyl]-L-alanyl]-L-proline 4-benzyloxybutyl ester (compound (IIc))

In the same manner as in Referential Example 5, 831 mg of the title compound was obtained as a colorless oily substance from 800 mg of the compound (VII) and 1.64 g of 4-benzyloxybutanol.

$^1$H-NMR (CDCl$_3$) δ: 1.24 (3H, d, J=6.6 Hz), 1.56-2.30 (11H, m), 2.55-2.75 (2H, m), 3.21-3.59 (6H, m), 4.01-4.20 (2H, m), 4.40-4.54 (1H, m), 4.49 (2H, s), 5.12 (1H, d, J=12.1 Hz), 5.18 (1H, d, J=12.1 Hz), 7.03-7.45 (15H, m). IR (neat) ν$_{max}$: 3448, 3324, 3061, 3029, 2952, 2869, 1740, 1648, 1496, 1454, 1422, 1362, 1277, 1182, 1095, 1055, 1029, 740, 699 cm$^{-1}$. [α]$_D$=−60.9° (CHCl$_3$, c:1.56)

Referential Example 8

1-[N-[(1S)-1-Benzyloxycarbonyl-3-phenylpropyl]-L-alanyl]-L-proline 2-methoxyethyl ester (compound (IId))

In the same manner as in Referential Example 5, 725 mg of the title compound was obtained as a colorless oily substance from 800 mg of the compound (VII) and 694 mg of 2-methoxyethanol.

$^1$H-NMR (CDCl$_3$) δ: 1.25 (3H, d, J=6.8 Hz), 1.79-2.33 (7H, m), 2.54-2.75 (2H, m), 3.22-3.73 (6H, m), 3.36 (3H, s), 4.15-4.33 (2H, m), 4.52 (1H, dd, J=3.7, 8.4 Hz), 5.13 (1H, d, J=12.1 Hz), 5.18 (1H, d, J=12.1 Hz), 7.07-7.44 (10H, m). IR (neat) ν$_{max}$: 3473, 3322, 3061, 3028, 2952, 2880, 1741, 1650, 1604, 1496, 1454, 1423, 1371, 1351, 1278, 1183, 1130, 1095, 1032, 751, 700 cm$^{-1}$. [α]$_D$=−77.8° (CHCl$_3$, c:1.06)

Referential Example 9

1-[N-[(1S)-1-Benzyloxycarbonyl-3-phenylpropyl]-L-alanyl]-L-proline 2-(2-methoxyethoxy)ethyl ester (compound (IIe))

In the same manner as in Referential Example 5, 675 mg of the title compound was obtained as a colorless oily substance from 720 mg of the compound (VII) and 986 mg of 2-(2-methoxyethoxy)ethanol.

$^1$H-NMR (CDCl$_3$) δ: 1.25 (3H, d, J=6.6 Hz), 1.80-2.30 (7H, m), 2.54-2.77 (2H, m), 3.29 (2H, t, J=6.6 Hz), 3.37 (3H, s), 3.40-3.76 (8H, m), 4.17-4.35 (2H, m), 4.36-4.57 (1H, m), 7.06-7.44 (5H, m). IR (neat) ν$_{max}$: 3481, 3321, 3061, 3028, 2952, 2928, 2878, 1741, 1646, 1454, 1423, 1366, 1278, 1184, 1112, 1047, 1030, 972, 917, 850 cm$^{-1}$. [α]$_D$=−71.1° (CHCl$_3$, c:1.02)

Referential Example 10

(R)-2-Hydroxy-4-phenylbutyric acid (compound (X))

(R)-2-Hydroxy-4-phenylbutyric acid ethyl ester (compound (IX)) (500 mg) was dissolved in ethanol (5.0 mL), and, at 0° C., a 10 w/v % aqueous sodium hydroxide solution (1.2 mL) was added dropwise thereto, followed by stirring for one hour at 0° C. The solvent was removed, and 1 mol/L hydrochloric acid was added dropwise to the residue at 0° C., to thereby adjust the pH of the mixture to 3, followed by extraction with diethyl ether. The obtained organic layer was washed with saturated brine and dried over anhydrous sodium sulfate, and the solvent was removed under reduced pressure, to thereby yield 412 mg of the title compound as a colorless powder.

m.p.: 104-107° C. $^1$H-NMR (CD$_3$OD) δ: 1.85-1.95 (1H, m), 1.97-2.11 (1H, m), 2.74 (2H, t, J=7.9 Hz), 4.08 (1H, dd, J=4.2, 8.3 Hz), 7.13-7.28 (5H, m). IR (KBr) ν$_{max}$: 3459, 2925, 1733, 1242, 1097, 695 cm$^{-1}$. [α]$_D$=−8.5° (MeOH, c:1.04)

Referential Example 11

(R)-2-Hydroxy-4-phenylbutyric acid benzyl ester (compound (XI))

The compound (X) (1.0 g) was dissolved in N,N-dimethylformamide (10 mL), and potassium bicarbonate (611 mg)

and benzyl bromide (660 μL) were added thereto at 0° C., followed by stirring for eight hours at 50° C. The solvent was removed, and water was added to the residue, followed by extraction with ethyl acetate. The obtained organic layer was washed with saturated brine and dried over anhydrous sodium sulfate, and the solvent was removed under reduced pressure. The obtained crude crystals were recrystallized from n-hexane, to thereby yield 1.1 g of the title compound as colorless crystals.

m.p.: 59-60° C. $^1$H-NMR (CDCl$_3$) δ: 1.89-2.00 (1H, m), 2.07-2.18 (1H, m), 2.63-2.81 (2H, m), 4.23 (1H, dd, J=4.0, 7.5 Hz), 5.16 (1H, d, J=12.7 Hz), 5.20 (1H, d, J=12.7 Hz), 7.14-7.20 (3H, m), 7.24-7.29 (2H, m), 7.35-7.39 (5H, m). IR (KBr) $v_{max}$: 3458, 2943, 1728, 1450, 1251, 1103, 699 cm$^{-1}$.

Referential Example 12

N-[(1S)-1-(Benzyloxycarbonyl)-3-phenyl]-L-alanine tert-butyl ester maleic acid salt (compound (XII))

The compound (XI) (2.0 g) was dissolved in dichloromethane (20 mL), and 2,6-lutidine (0.94 mL) and trifluoromethanesulfonic anhydride (1.4 mL) were added thereto at 0° C., followed by stirring for two hours at 0° C. Chloroform was added to the reaction mixture, and the resultant mixture was washed with a 5 w/v % aqueous potassium bisulfate solution and saturated aqueous sodium bicarbonate solution. The obtained organic layer was washed with saturated brine and dried over anhydrous sodium sulfate. The solvent was removed under reduced pressure, to thereby yield 3.5 g of 2-trifluoromethanesulfonyloxy-4-phenylbutyric acid benzyl ester as a brown viscous substance. An L-alanine tert-butyl ester hydrochloride (2.0 g) was dissolved in water (20 mL), and ammonium carbonate (1.7 g) and a nitromethane solution (15 mL) of 2-trifluoromethanesulfonyloxy-4-phenylbutyric acid benzyl ester (3.5 g) were added to the solution, followed by stirring for three hours at 50° C. Ethyl acetate was added to the reaction mixture, and the resultant mixture was washed with a 5 w/v % aqueous potassium bisulfate solution, saturated aqueous sodium bicarbonate solution, water, and saturated brine. The mixture was dried over anhydrous sodium sulfate, and the solvent was removed under reduced pressure. The residue was dissolved in ethyl acetate (14 mL), and maleic acid (859 mg) was added thereto, followed by heating under reflux. After the crystals were completely dissolved, the solution was gradually cooled to room temperature, to thereby yield crude crystals of the title compound. The crude crystals were recrystallized from ethyl acetate, to thereby yield 2.63 g of the title compound as colorless crystals.

m.p.: 137-138° C. $^1$H-NMR (CDCl$_3$) δ: 1.44 (9H, s), 1.48 (3H, d, J=7.2 Hz), 2.24 (2H, t, J=7.3 Hz), 2.60-2.79 (2H, m), 3.69 (1H, q, J=7.2 Hz), 3.77 (1H, t, J=6.2 Hz), 5.20 (1H, d, J=11.9 Hz), 5.27 (1H, d, J=11.9 Hz), 6.34 (1H, s), 7.08-7.10 (2H, m), 7.18-7.28 (3H, m), 7.38-7.39 (5H, m). IR (KBr) $v_{max}$: 2987, 1746, 1458, 1352, 1162, 996, 697 cm$^{-1}$. $[α]_D$=-1.43° (CHCl$_3$, c:1.38)

Referential Example 13

N-[(1S)-1-(Benzyloxycarbonyl)-3-phenyl]-L-alanine (compound (XIII))

Water was added to compound (XII) (2.5 g), and the pH of the mixture was adjusted to 8 with saturated aqueous sodium bicarbonate solution, followed by extraction with ethyl acetate. The obtained organic layer was washed with saturated brine and dried over anhydrous sodium sulfate. The solvent was removed under reduced pressure, and a hydrogen chloride-dioxane solution (45 mL) was added dropwise thereto, followed by stirring for 13 hours at room temperature. The solvent was removed under reduced pressure, water was added thereto, and the pH of the mixture was adjusted to 6 with saturated aqueous sodium bicarbonate solution. The formed precipitate was collected through filtration and then recrystallized from ethyl acetate, to thereby yield 1.5 g of the title compound as a colorless powder.

m.p.: 160-161° C. $^1$H-NMR (CD$_3$OD) δ: 1.48 (3H, d, J=7.2 Hz), 2.14-2.21 (2H, m), 2.52-2.62 (1H, m), 2.67-2.77 (1H, m), 3.57 (1H, q, J=7.2 Hz), 4.05 (1H, t, J=6.1 Hz), 5.18 (1H, d, J=11.9 Hz), 5.36 (1H, d, J=11.9 Hz), 7.08-7.27 (5H, m), 7.36-7.45 (5H, m). IR (KBr) $v_{max}$: 2781, 1739, 1618, 1356, 1262, 1192, 698 cm$^{-1}$ $[α]_D$=-6.6° (MeOH, c:1.10)

Referential Example 14

L-Proline 3-benzyloxypropyl ester oxalate (compound (XIV))

L-Proline (2.30 g) was dissolved in benzene (20 mL), and p-toluenesulfonic acid monohydrate (4.57 g) and 3-benzyloxypropanol (1.58 mL) was added thereto, followed by stirring for 15 hours under reflux while generated water was removed by azeotropy. The solvent was removed, and saturated aqueous sodium bicarbonate solution was added thereto, followed by extraction with chloroform. The extract was washed with saturated brine and dried over anhydrous sodium sulfate. The solvent was removed under reduced pressure, and the residue was dissolved in ethyl acetate (16 mL). Oxalic acid (693 mg) was dissolved in the solution under heating, and the resultant solution was left to stand at room temperature. The formed crystals were collected through filtration and then recrystallized from ethyl acetate, to thereby yield 1.92 g of the title compound as a colorless powder.

m.p.: 84-85° C. $^1$H-NMR (CDCl$_3$) δ: 1.90-2.11 (5H, m), 2.13-2.45 (1H, m), 3.41-3.50 (1H, m), 3.52 (2H, t, J=6.0 Hz), 4.24-4.39 (2H, m), 4.43-4.51 (1H, m), 4.48 (2H, s), 7.30-7.38 (5H, m). IR (KBr) $v_{max}$: 3348, 2873, 1742, 1637, 1560, 1458, 1402, 1279, 1229, 1108, 720, 497 cm$^{-1}$ $[α]_D$=-28.7° (CHCl$_3$, c:1.17)

Referential Example 15

1-[N-[(1S)-1-Benzyloxycarbonyl-3-phenylpropyl]-L-alanyl]-L-proline 3-benzyloxypropyl ester (compound (IIb))

The compound (XIV) (500 mg) was dissolved in water (6 mL), and the pH of the solution was adjusted to 8 with saturated aqueous sodium bicarbonate solution, followed by extraction with chloroform. The obtained organic layer was washed with saturated brine and dried over anhydrous sodium sulfate. The solvent was removed under reduced pressure, and the residue was dissolved in chloroform (7 mL). At 0° C., the compound (XIII) (483 mg), N,N'-dicyclohexylcarbodiimide (291 mg), and 1-hydroxy-1H-benzotriazole monohydrate (237 mg) were added to the solution. The temperature of the solution was gradually increased from 0° C. to room temperature, and the solution was stirred for 23 hours at room temperature. The reaction mixture was washed with a 5 w/v % aqueous potassium hydrogensulfate solution, saturated aqueous sodium bicarbonate solution, water, and saturated brine, and subsequently dried over anhydrous sodium sulfate. The solvent was removed, and the residue was purified by silica gel column chromatography (hexane:ethyl acetate=2:3 to 1:2), to thereby yield 747 mg of the title compound as a colorless oily substance.

Example 1

1-[N-[(1S)-1-Carboxy-3-phenylpropyl]-L-alanyl]-L-proline 2-hydroxyethyl ester (Inventive Compound 1)

The compound (IIa) (2.65 g) was dissolved in ethanol (100 mL), 5 mass % palladium carbon (1.3 g) was added to the solution, followed by stirring for 13 hours at room temperature under hydrogen atmosphere (4 atm). The catalyst was removed by filtration with Celite, and the filtrate was condensed under reduced pressure. The residue was purified through silica gel column chromatography (chloroform:methanol=3:1), to thereby yield 1.49 g of the title compound as a colorless amorphous substance.
$^1$H-NMR (CDCl$_3$) δ: 1.47 (3H, d, J=6.8 Hz), 1.80-2.36 (6H, m), 2.60-2.83 (2H, m), 3.27-3.95 (6H, m), 3.96-4.57 (4H, m), 6.97-7.22 (5H, m). IR (KBr) $v_{max}$: 3422, 3028, 2956, 2879, 1742, 1655, 1560, 1543, 1509, 1498, 1451, 1388, 1282, 1187, 1087, 1051, 895, 861, 753, 702 cm$^{-1}$. MS m/z (ESI+): 393 (M+H)$^+$. [α]$_D$=−26.4° (CHCl$_3$, c:1.20)

Example 2

1-[N-[(1S)-1-Carboxy-3-phenylpropyl]-L-alanyl]-L-proline 3-hydroxypropyl ester (Inventive Compound 2)

In the same manner as in Example 1, 2.06 g of the title compound was obtained as a colorless amorphous substance from 2.97 g of the compound (IIb).
$^1$H-NMR (CDCl$_3$) δ: 1.55 (3H, d, J=7.0 Hz), 1.78-2.38 (8H, m), 2.65-2.87 (2H, m), 3.31 (1H, t, J=7.0 Hz), 3.36-3.80 (5H, m), 4.00-4.15 (1H, m), 4.17-4.39 (2H, m), 4.47-4.60 (1H, m), 7.07-7.28 (5H, m). IR (KBr) $v_{max}$: 3385, 3027, 2958, 2878, 1741, 1655, 1560, 1543, 1509, 1498, 1439, 1388, 1280, 1186, 1093, 1053, 920, 863, 751, 702 cm$^{-1}$. MS m/z (ESI+): 407 (M+H)$^+$. [α]$_D$=−33.0° (CHCl$_3$, c:1.04)

Example 3

1-[N-[(1S)-1-Carboxy-3-phenylpropyl)-L-alanyl]-L-proline 4-hydroxybutyl ester (Inventive Compound 3)

In the same manner as in Example 1, 2.92 g of the title compound was obtained as a colorless amorphous substance from 4.51 g of the compound (IIc).
$^1$H-NMR (CDCl$_3$) δ: 1.35-2.31 (10H, m), 1.49 (3H, d, J=6.8 Hz), 2.63-2.83 (2H, m), 3.33 (1H, t, J=6.8 Hz), 3.38-3.77 (5H, m), 3.88-4.55 (4H, m), 7.00-7.24 (5H, m). IR (KBr) $v_{max}$: 3386, 3028, 2953, 2874, 1742, 1656, 1451, 1382, 1281, 1214, 1184, 1093, 1046, 944, 859, 752, 701 cm$^{-1}$. MS m/z (ESI+): 421 (M+H)$^+$. [α]$_D$=−32.9° (CHCl$_3$, c:1.31).

Example 4

1-[N-[(1S)-1-Carboxy-3-phenylpropyl]-L-alanyl]-L-proline 2-methoxyethyl ester (Inventive Compound 4)

The compound (IId) (700 mg) was dissolved in ethanol (4.0 mL), and 5 mass % palladium carbon (140 mg) was added to the solution, followed by stirring for one hour at room temperature under hydrogen atmosphere (normal pressure). The catalyst was removed through filtration with Celite, and the filtrate was condensed under reduced pressure. The residue was purified by silica gel column chromatography (chloroform:methanol=20:1), to thereby yield 547 mg of the title compound as a colorless amorphous substance.
$^1$H-NMR (CDCl$_3$) δ: 1.45 (3H, d, J=7.0 Hz), 1.86-2.35 (6H, m), 2.64-2.86 (2H, m), 3.25 (1H, t, J=7.0 Hz), 3.36 (3H, s), 3.42-3.69 (4H, m), 3.82 (1H, q, J=6.8 Hz), 4.15-4.43 (2H, m), 4.54 (1H, dd, J=3.5, 8.3 Hz), 7.06-7.25 (5H, m). IR (KBr) $v_{max}$: 3448, 3028, 2954, 2882, 1743, 1655, 1560, 1543, 1523, 1509, 1498, 1450, 1380, 1280, 1185, 1129, 1094, 1034, 916, 865, 753, 702 cm$^{-1}$. MS m/z (ESI+): 407 (M+H)$^+$. [α]$_D$=−44.5° (CHCl$_3$, c:1.10)

Example 5

1-[N-[(1S)-1-Carboxy-3-phenylpropyl]-L-alanyl]-L-proline 2-(2-methoxyethoxy)ethyl ester (Inventive Compound 5)

In the same manner as in Example 4, 465 mg of the title compound was obtained as a colorless amorphous substance from 640 mg of the compound (IIe).
$^1$H-NMR (CDCl$_3$) δ: 1.43 (3H, d, J=6.8 Hz), 1.87-2.32 (6H, m), 2.64-2.85 (2H, m), 3.22 (1H, t, J=6.4 Hz), 3.37 (3H, s), 3.43-3.80 (8H, m), 4.17-4.45 (2H, m), 4.55 (1H, dd, J=3.5, 8.3 Hz), 7.09-7.28 (5H, m). IR (KBr) $v_{max}$: 3448, 3027, 2930, 2880, 1742, 1655, 1560, 1543, 1523, 1509, 1498, 1451, 1382, 1281, 1187, 1139, 1109, 1048, 919, 859, 752, 703 cm$^{-1}$. MS m/z (ESI+): 451 (M+H)$^+$. [α]$_D$=−41.1° (CHCl$_3$, c:1.05)

Example 6

Stability Test

About 5 mg of each of Inventive Compounds 1 to 5 and enalapril was put in a glass vial. Isopropyl myristate (100 μL) was added, to thereby yield a solution (or suspension). The vial was tightly sealed and stored in a 60° C. thermostatic chamber for one week. Methanol was added to the solution contained in the vial until the total volume of the solution mixture became 100 mL. The resultant solution was employed as a test solution to be subjected to an HPLC analysis. Peak area ratio (expressed by percentage) of each compound with respect to a sum of all the obtained peak areas was calculated. The calculation show that, as summarized in Table 1, enalapril had been completely degraded into its corresponding closed-ring product or other degraded products over the storage term of one week, whereas the Inventive Compounds exhibited good stability.

TABLE 1

| | | Area ratio (%): storage at 60° C. for 1 week | | | | |
|---|---|---|---|---|---|---|
| Compound | | Proline ester compound | Enalapril | Enalaprilat | Closed ring product | Other degraded products |
| Inventive Compound | 1 | 91.8 | — | 0.0 | 0.0 | 8.2 |
| | 2 | 96.7 | — | 0.0 | 0.0 | 3.3 |
| | 3 | 94.4 | — | 0.0 | 0.0 | 5.6 |
| | 4 | 99.1 | — | 0.0 | 0.0 | 0.9 |
| | 5 | 94.2 | — | 0.0 | 0.0 | 5.8 |
| Comp. Example | Enalapril | — | 0.0 | 0.0 | 48.4 | 51.6 |

Example 7

Metabolism Test by Use of Cultured Human Skin

A sample of a three-dimensional cultured human skin model (LSE-high, Toyobo Co., Ltd.) was set in a vertical diffusion cell whose temperature was maintained at 37° C., and the receptor phase of the cell was filled with 7 mL isotonic phosphate buffer (PBS, pH 7.4). The cell was allowed to stand for one hour. Each of Inventive Compounds 1 to 3 and enalapril (serving as a Comparative Example) was dissolved or suspended in isopropyl myristate so as to attain a concentration of 1.0 mass %. The solution (200 µL) was applied to the skin sample, whereby the test started. When 24 hours had passed after the test started, the concentrations of proline esters or enalapril (i.e., a prodrug of enalaprilat) which remained unchanged, and the transformed product enalaprilat contained in PBS in the receptor phase were determined through HPLC. From the obtained data, concentration ratio of "proline esters or enalapril": "enalaprilat" was calculated (presence ratio). As shown in Table 2, of the proline esters which permeated the three-dimensional cultured human skin model, 64 to 77% was converted to enalaprilat.

TABLE 2

| | Presence ratio[a] |
|---|---|
| Inventive Compound 1 | 23.5/76.5 |
| Inventive Compound 2 | 36.3/63.7 |
| Inventive Compound 3 | 30.4/69.6 |
| Enalapril (Comp. Ex.) | 98.8/1.2 |

[a] Concentration ratio (proline ester or enalapril/enalaprilat)

Example 8

Production of Patches

Styrene-isoprene-styrene block copolymer (trade name; Quintac 3421, product of Zeon Corporation) (30 g) and a tackifying resin (an aliphatic saturated hydrocarbon resin, trade name: Quintone M100, product of Zeon Corporation) (60 g) were dissolved in toluene (110 g), and liquid paraffin (10 g) was added thereto, followed by further mixing so as to form a uniform solution, to thereby prepare an adhesive solution. The adhesive solution (65 mass %) was mixed with Inventive Compound 1 (20 mass %), isopropyl myristate (10 mass %), and lauromacrogol (5 mass %), the "mass %" being based on dried solid content of the formed coating. The viscosity of the mixture was adjusted with toluene, followed by mixing so as to form a uniform solution. The drug-containing adhesive solution was applied through use of a film applicator to the silicone-coated side of a peelable polyethylene terephthalate sheet (thickness 75 µm) so that the formed coating has a thickness of 200 µm. The product was dried for ten minutes at approximately 65° C., and a polyethylene terephthalate support (thickness 12 µm) was affixed to the coating surface. The product was cut into pieces having predetermined dimensions, to thereby prepare patch 1.

Similarly, Inventive Compounds 2 to 5 were processed, thereby preparing patches 2 to 5, respectively.

Hairless Mouse Skin Permeability Test

A portion of the skin was extirpated from of each male hairless mouse (5 weeks old, body weight: about 20 g) and placed in a vertical diffusion cell maintained at 37° C. PBS (pH 7.2, 7 mL) was charged to the receptor phase, and the skin sample was allowed to stand for one hour. Each of the patches 1 to 5 was punched out, to thereby provide patch pieces (1.33 cm$^2$). Each patch piece was attached to each skin sample, whereby the test was started. PBS (0.5 mL) from the receptor phase was sampled hourly, from the start of the test to hour 8. Thereafter, the sampling was performed every two hours to hour 24. After each sampling was complete, PBS was replenished to the receptacle in the same amount as the sampled PBS. Each of the PBS sample collected from the receptacle was analyzed through HPLC so as to determine the concentrations of unchanged proline esters (i.e., prodrugs of enalaprilat) and transformed product enalaprilat. The determined proline ester concentration was regarded as an enalaprilat concentration, and total enalaprilat concentration was calculated through addition of two enalaprilat concentrations. The total concentration was plotted with respect to permeation time. From the obtained permeation profile, skin permeation rate (flux) was determined from the slope of the curve in a region where permeation rate was in a steady state. In addition, permeation delay time (Lag time) and 24-hour-cumulative permeation amount per unit patch area (1 cm$^2$) were also calculated. The concentration (in PBS in the receptacle) ratio of proline ester: enalaprilat 24 hours after the start of the test was determined, thereby serving as presence ratio of proline ester: enalaprilat. As shown in Table 3, the percutaneous preparation containing a proline ester of the present invention exhibited excellent skin permeability, and the proline ester permeated the skin was converted to enalaprilat in a proportion of about 50 to 85%.

TABLE 3

| Tape form drug | Skin Permeation rate (μg/cm²/hr) | Permeation delay time (hr) | Presence ratio[a] | Cumulative permeation amount (μg/cm²) |
|---|---|---|---|---|
| Patch 1 | 21.80 | 3.60 | 50.5/49.5 | 393.39 |
| Patch 2 | 25.03 | 2.59 | 29.3/70.7 | 443.64 |
| Patch 3 | 17.30 | 2.40 | 41.9/58.1 | 374.31 |
| Patch 4 | 6.14 | 4.20 | 20.2/79.8 | 88.88 |
| Patch 5 | 11.59 | 2.30 | 15.0/85.0 | 187.10 |

[a] Concentration ratio (proline ester/enalaprilat)

What is claimed is:

1. A proline ester represented by the following formula (I):

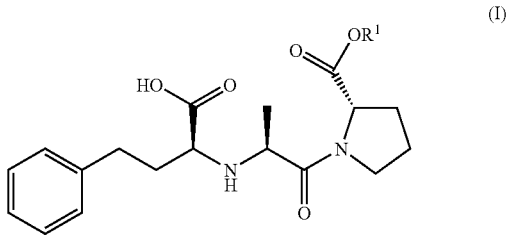

wherein $R^1$ represents a hydroxy-lower alkyl group, a lower alkoxy-lower alkyl group, or a lower alkoxy-lower alkoxy-lower alkyl group or a pharmaceutically acceptable salt thereof.

2. The proline ester as described in claim 1, which is selected from the group consisting of 1-[N-[(1S)-1-Carboxy-3-phenylpropyl]-L-alanyl]-L-proline 2-hydroxyethyl ester, 1-[N-[(1S)-1-Carboxy-3-phenylpropyl]-L-alanyl]-L-proline 3-hydroxypropyl ester, 1-[N-[(1S)-1-Carboxy-3-phenylpropyl]-L-alanyl]-L-proline 4-hydroxybutyl ester, 1-[N-[(1S)-1-Carboxy-3-phenylpropyl]-L-alanyl]-L-proline 2-(2-methoxyethoxy)ethyl ester, and 1-[N-[(1S)-1-Carboxy-3-phenylpropyl]-L-alanyl]-L-proline 2-methoxyethyl ester, or a pharmaceutically acceptable salt thereof.

3. A drug comprising a proline ester as recited in claim 1 or a pharmaceutically acceptable salt thereof, and a pharmaceutically acceptable carrier.

4. A percutaneous preparation comprising a proline ester as recited in claim 1 or a pharmaceutically acceptable salt thereof, and a pharmaceutically acceptable carrier.

5. The percutaneous preparation as described in claim 4, which is a patch.

6. The percutaneous preparation as described in claim 4, which comprises one or more percutaneous absorption enhancers selected from the group consisting of a fatty acid ester and a non-ionic surfactant.

7. The percutaneous preparation as described in claim 6, wherein the percutaneous absorption enhancer is selected from the group consisting of isopropyl myristate, lauromacrogol, lauric acid diethanolamide, glyceryl monocaprylate, glyceryl monolaurate, sorbitan monocaprylate, and polyoxyethylene sorbitan monooleate.

8. A method for treating a pathological condition affected or induced by activation of an ACE comprising:
administering to a subject in need thereof an effective amount of a proline ester of claim 1 or a pharmaceutically acceptable salt thereof;
wherein the pathological condition is selected from the group consisting of hypertension, a cardiac disease selected from the group consisting of cardiac hypertrophy, cardiac failure, and myocardial infarct.

9. The method of claim 8, wherein administration is performed percutaneously.

10. The proline ester of claim 1, wherein $R^1$ represents a hydroxy-lower alkyl group.

11. The proline ester of claim 1, wherein $R^1$ represents a lower alkoxy-lower alkyl group.

12. The proline ester of claim 1, wherein $R^1$ represents a lower alkoxy-lower alkoxy-lower alkyl group.

* * * * *